(12) United States Patent
Abbas et al.

(10) Patent No.: US 9,526,240 B2
(45) Date of Patent: Dec. 27, 2016

(54) SPRAYABLE DISPERSED STARCH-BASED BIOPLASTIC FORMULATION TO CONTROL PESTS

(71) Applicants: The United States of America, as Represented by the Secretary of Agriculture, Washington, DC (US); Alma Mater Studiorum—Università di Bologna, Bologna (IT)

(72) Inventors: Hamed K Abbas, Greenville, MS (US); Cesare Accinelli, Bologna (IT)

(73) Assignees: The United States of America, as Represented by the Secretary of Agriculture, Washington, DC (US); Alma Mater Studiorum-Universita di Bologna, Bologna (IT)

( * ) Notice: Subject to any disclaimer, the term of this patent is extended or adjusted under 35 U.S.C. 154(b) by 0 days.

(21) Appl. No.: 14/276,224

(22) Filed: May 13, 2014

(65) Prior Publication Data
US 2015/0327540 A1    Nov. 19, 2015

(51) Int. Cl.
| | |
|---|---|
| *A01N 63/00* | (2006.01) |
| *A01N 25/10* | (2006.01) |
| *A01N 63/04* | (2006.01) |
| *A01N 43/16* | (2006.01) |
| *A01N 63/02* | (2006.01) |

(52) U.S. Cl.
CPC ............ *A01N 25/10* (2013.01); *A01N 43/16* (2013.01); *A01N 63/02* (2013.01); *A01N 63/04* (2013.01)

(58) Field of Classification Search
CPC .................................. A01N 63/00; A01N 3/00
See application file for complete search history.

(56) References Cited

U.S. PATENT DOCUMENTS 5,990,389 A * 11/1999 Rao et al. .................. 800/301
8,173,179 B1 * 5/2012 Abbas et al. ............... 424/725

OTHER PUBLICATIONS

Accinelli et al., "Use of a granular bioplastic formulation for carrying conidia of a non-aflatoxigenic strain of Aspergillus flavus," Bioresource Technology 100:3997-4004, 2009.*

* cited by examiner

*Primary Examiner* — Rosanne Kosson
(74) *Attorney, Agent, or Firm* — John D. Fado; Evelyn M. Rabin

(57) ABSTRACT

A sprayable liquid biodegradable formulation comprising biocontrol microorganisms imbedded in a dispersed starch-based bioplastic is effective for delivering biocontrol microorganisms and bioactive compounds to soil, crops and seeds and facilitating positioning of biocontrol agents in close proximity to target pests. After application with conventional spray equipment, water evaporates rapidly and the dispersed bioplastic formula remains, serving as a prolonged growth substrate for the biocontrol microorganisms. Application of the bioplastic dispersion formulation comprising *Beauveria bassiana* significantly reduced damages caused by the European Corn Borer in corn and the Tarnished Plant Bug in cotton. Applying a formulation of spores of a non-aflatoxigenic *A. flavus* isolate resulted in a 97% reduction of aflatoxin contamination of corn. The bioplastic dispersion formulation is effective in delivering crystal *Bacillus thuringiens* endotoxins to European Corn Borer larvae, causing 72% mortality. The sprayable bioplastic formulation protects seeds from soil-borne pathogens, thereby reducing damping-off in tomato plants by up to 85%.

13 Claims, 10 Drawing Sheets

SPRAYABLE DISPERSED STARCH-BASED BIOPLASTIC FORMULATION TO CONTROL PESTS

BACKGROUND OF THE INVENTION

1. Field of the Invention

This invention relates to a sprayable liquid biocontrol formulation comprising dispersed starch-based bioplastic imbedded with microbial biocontrol agents which is delivered to targets, such as pathogens and foliage, to decrease contamination and infestation of agricultural products. The present invention provides examples of spraying the biocontrol formulation comprising an entomopathogenic isolate of *Beauveria bassiana* or an endotoxin produced by *Bacillus thuringiensis* to effectively control infestation in corn by the European Corn Borer, delivering the sprayable biocontrol formulation comprising a non-toxigenic *Aspergillus flavus* strain to crops to effectively reduce aflatoxin contamination in corn and other crop plants, and to applying the sprayable biocontrol formulation comprising *Trichoderma harzianum* to tomato seeds to effectively reduce damping off. Additionally, this sprayable bioplastic formulation is also used for carrying spores of a *Beauveria bassiana* strain for controlling the Tarnished Plant Bug in cotton.

2. Description of the Relevant Art

The general term microbial biocontrol agents refers to the use of microorganisms in the control of agricultural pests, including bacteria, fungi, weeds and insects. Although the literature reports many examples of effective microbial isolates for controlling specific pests or plant pathogens under laboratory or small-scale field conditions, only a limited number have entered into the marketplace. A large number of factors may influence the performance of microbial biocontrol agents given that they are living organisms, different from synthetic agrochemicals. In several cases, lack of consistent field efficacy, high production costs, and product variability have limited their commercial success (Glare et al. 2012. *Trends in Biotech.* 30:250-258). However, the most important factor limiting the practical use of microbial biocontrol agents in agriculture is related to how these biocontrol microorganisms are formulated (Legget et al. 2011. *Can. J. Plant Pathol.* 33:101-107). Other than serving for delivering microbial biocontrol agents to the target (i.e. soil or foliage), formulation should also guarantee adequate shelf life, easy handling and safety to operators, and prolonged bioactivity of biocontrol microorganisms after field application (Fravel, D. R. 2009. *Annu. Rev. Phytopathol.* 43:337-359; Legget et al., supra). Inadequate or inappropriate formulation is consequently the most common reason limiting the use and diffusion of microbial biocontrol agents in agriculture (Kaewchai et al. 2009. *Fungal Diversity* 38:25-50). Recently, advancement in biotechnology and applied biology, and the increasing demand for safety of food products and environmental sustainability, have resulted in an increased demand for effective microbial biocontrol agents and consequently the development of new technical approaches (Leggett et al., supra; Glare et al., supra).

As mentioned above, microbial biocontrol agents are mainly represented by bacteria or fungi which are used for controlling pests, plant pathogens and weeds in agriculture. In addition to the bacterium *Bacillus thuringiensis*, other successful examples of biocontrol agents are the fungi *Trichoderma* spp. and *Beauveria bassiana* (Kaewchai et al., supra; Glare et al., supra). These two filamentous fungi are formulated in a variety of different delivery systems, comprising pre-gelatinized starch-flour, granules of semolina flour and clay, inoculated grains, wettable powder, etc. (Papavizas 1985. *Annu. Rev. Phytopathol.* 23:23-54; Daigle and Cotty 1997. *Biocontrol Sci. Technol.* 7:3-10; Harman et al. 2011. *Phytoparasitica.* 39:103-108).

Many other biocontrol fungi, including atoxigenic isolates of the fungus *A. flavus*, which are currently being used for reducing aflatoxin contamination in corn, cotton and peanuts, are formulated following similar techniques and approaches, (Dorner, J. W. 2004. *Toxin Rev.* 23:425-450; Abbas et al. 2006. *Biocontrol Sci. Technol.* 16:437-449). Aflatoxins refer to a group of carcinogenic mycotoxins mainly produced by the soil-inhabiting fungus *A. flavus*. An innovative and successful approach for reducing aflatoxin contamination in corn is a biocontrol strategy consisting of the use of atoxigenic isolates of *A. flavus* to competitively exclude indigenous aflatoxigenic isolates. Studies conducted in Southern USA have demonstrated that soil application of cereal grains inoculated with atoxigenic isolates of *A. flavus* were successful in reducing aflatoxin contamination in corn, cotton and peanuts (Dorner, J. W, supra; Abbas et al., supra). In addition, a biocontrol formulation consisting of spore-coated barley seeds has been commercialized in the USA. More recent studies have shown that cereal grains can be efficiently replaced by granules made of the starch-based bioplastic Mater-Bi™ (MB) (Accinelli et al. 2009. *Bioresource Technol.* 100: 3997-4004; Accinelli et al. 2012. *Crop Protection* 32:30-35; Abbas et al. 2012. U.S. Pat. No. 8,173,179). Similar to *A. flavus*, a variety of other filamentous fungi are capable of growing on starch-rich substrates (Accinelli and Abbas. 2011. *Toxin Rev.* 30:71-78). Consequently, the concept of using a starch-based bioplastic matrix to deliver fungal propagules has been extended to the biocontrol fungus *Trichoderma* spp. (Abbas et al. 2012. US Published Application No. 20120213740; Accinelli et al. 2014. *Acta Hort.* 1015:79-88).

The original concept consisted of a granular starch-based bioplastic formulated to serve as a carrier matrix to sustain growth of soil-born biocontrol fungi and to provide a mechanism for inoculation of corn field soil. The bioplastic granules are composed of starch-based polymers stabilized by chemical cross linking. Bioplastic granules promote intense fungal growth and sporulation which results in rapid soil colonization. In addition, bioplastic granules are produced from renewable and compostable sources.

Various biocontrol methods and formulations for effective control of toxigenic fungi and bacteria and insect pests are known in the art, as discussed above. However, there still remains a need for formulations of biocontrol agents which are effective for ensuring the integrity and effectiveness of the biocontrol agent after long term storage, and for facilitating handling, safety, timing and positioning of application of the biocontrol agent in the field and in the greenhouse. The need for suitable, effective formulation systems to deliver other biological control agents is also evident.

SUMMARY OF THE INVENTION

We have invented a sprayable liquid biocontrol formulation comprising biocontrol microorganisms imbedded in a bioplastic dispersion prepared from the commercial bioplastic Mater-Bi™.

In accordance with this discovery, it is an object of the invention to provide a sprayable microbial biocontrol agent composition comprising biocontrol microorganisms imbedded in a dispersed starch-based bioplastic.

It is further object of the invention to provide a sprayable microbial biocontrol agent composition comprising non-toxigenic strains of *Aspergillus* spp. or other related species imbedded in a bioplastic dispersion.

It is another object of the invention to provide a sprayable biocontrol composition comprising the non-toxigenic *A. flavus* strain NRRL 30797 imbedded in a Mater-Bi™ bioplastic dispersion.

It is still further object of the invention to provide a sprayable biocontrol composition comprising a *Trichoderma harzianum* strain imbedded in dispersed Mater-Bi™ bioplastic capable of suppressing damping-off disease.

It is an additional object of the invention to provide a sprayable biocontrol composition comprising a *Trichoderma virens* strain imbedded in dispersed Mater-Bi™ bioplastic capable of suppressing damping-off disease.

It is another object of the invention to provide a sprayable biocontrol composition capable of controlling infestation by the European Corn Borer (*Ostrinia nubilalis*) comprising an isolate of *Beauveria bassiana* or an endotoxin produced by *Bacillus thuringiensis* imbedded in dispersed Mater-Bi™ bioplastic.

It is another object of the invention to provide a sprayable biocontrol composition capable of controlling infestation by the Tarnished Plant Bug (*Lygus lineoraris*) comprising an isolate of *Beauveria bassiana* imbedded in Mater-Bi™ bioplastic dispersion.

It is yet another object of the invention to provide a biocontrol method of preventing or reducing aflatoxin contamination of corn which includes spraying the sprayable biocontrol composition of dispersed Mater-Bi™ imbedded with a non-toxigenic *A. flavus* strain onto plants to control aflatoxin.

It is an additional object of the invention to provide a biocontrol method of suppressing damping-off disease which includes spraying the sprayable biocontrol composition comprising *T. harzianum* imbedded in a Mater-Bi™ bioplastic dispersion onto soil, plants or plant parts.

It is an additional object of the invention to provide a biocontrol method of suppressing damping-off disease which includes spraying the sprayable biocontrol composition comprising *T. virens* imbedded in a Mater-Bi™ bioplastic dispersion with onto soil, plants or plant parts.

It is a further object of the invention to provide a biocontrol method of controlling infestation by the European Corn Borer comprising spraying the sprayable biocontrol composition comprising a Mater-Bi™ bioplastic dispersion imbedded with an isolate of *Beauveria bassiana* or with an endotoxin produced by *B. thuringiensis* onto corn plants.

It is a further object of the invention to provide a biocontrol method of controlling infestation by the Tarnished Plant Bug comprising spraying the sprayable biocontrol composition comprising a Mater-Bi™ bioplastic dispersion imbedded with an isolate of *Beauveria bassiana*.

Also part of this invention is a kit, comprising the sprayable biocontrol compositions comprising dispersed Mater-Bi™ bioplastic imbedded with microbial biocontrol agents.

Other objects and advantages of this invention will become readily apparent from the ensuing description.

DETAILED DESCRIPTION OF THE INVENTION

We have demonstrated that a novel sprayable bioplastic dispersion formulation for a biocontrol composition comprising biocontrol microorganisms imbedded in a Mater-Bi™ bioplastic dispersion is effective for introducing a stable population of the biocontrol microorganism into soil or onto the foliage or other parts of plants.

The sprayable formulation is obtained by homogenizing different types of bioplastic matrices, e.g., granules, pellets, powder, in water, which is then enriched with fungal structures such as spores, cells, mycelium, etc., bacterial cells or other bioactive compounds (e.g., endotoxins). Alternatively, inoculation of the bioplastic powder can also be achieved by solid state fermentation processes where the bioplastic and, e.g., a fungal culture, are incubated together in a receptacle such as an autoclavable bag for 3-7 days, then dried in an oven at 45° C. The resulting dried material is ground into flour which is dispersible in water and sprayable. Another procedure includes passing the bioplastic matrices (e.g., pellets or granules) through an extruder equipped with small-size (<1 mm) nozzles. Extrusion can be achieved using a conventional industrial extruder or a bench-top extruder. Resulting powder is directly dispersed in water containing microbial structures (e.g., spores, mycelium, cells) or bioactive compounds. The novelty of this concept is that it combines the plastic properties of the formulation with biocontrol organisms or bioactive substances.

To better sustain the growth of biocontrol microbial agents, specific nutrients can be also added to the mixture, made by either process of formulation, before field application. Inoculated bioplastic powder is suspended in water before field application, which uses a conventional pesticide spray machine. Water suspension of microorganism/bioplastic mixtures can also be sprayed on the seed surface for protecting seedlings against damping-off and other diseases.

Figure 1:
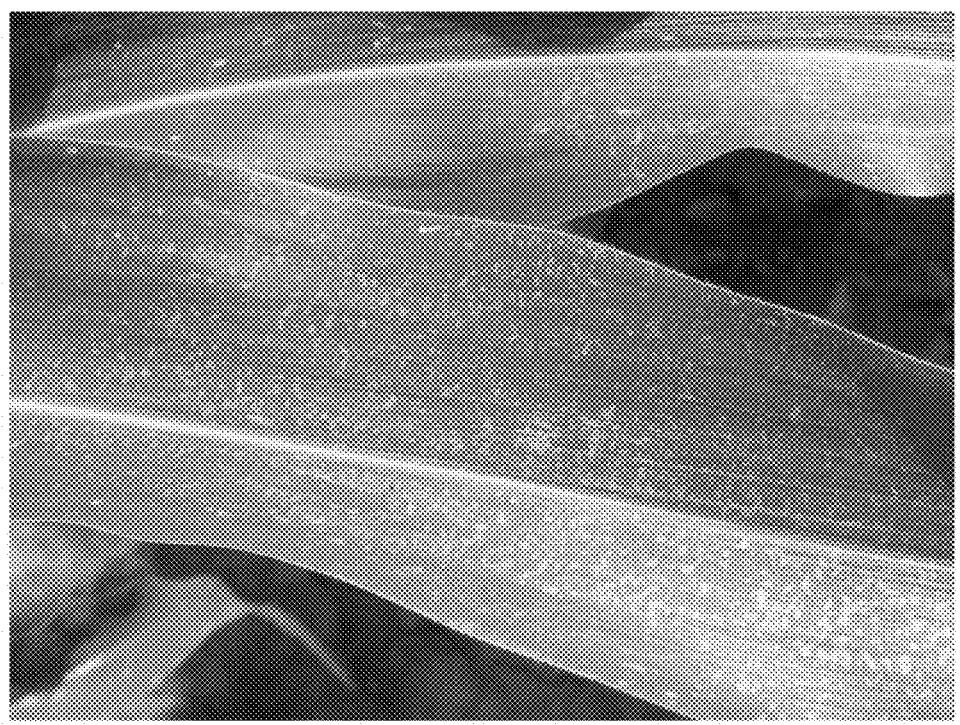
FIG. 1 shows the surface of corn leaves after applying the sprayable biocontrol formulation comprising dispersed starch-based bioplastic.

Because of the plastic properties of the sprayable formulation, once the biocontrol formulation is applied by spraying to plant foliage or other plant organs, for example, seeds, water is rapidly removed by evaporation and a contiguous film or thin layer or spots of the bioplastic formula containing selected microorganisms remains adhering to the leaf surface for long periods (up to 2-4 months), where it serves as a growth substrate for the biocontrol microorganisms and a durable control of pests. Because of the property of the film adhering, i.e., sticking to the foliage, no adhesive has to be added to the formulation (FIG. 1). Further, the bioplastic is not just a carrier; it is a food source for the biocontrol microorganisms. The bioplastic also retards break down; therefore, the composition is durable and lasts.

The novel sprayable bioplastic formulation concept and technology offers advantages over the granular bioplastic formulations and other formulations. Advantages include more flexibility in the timing of applications, prolongation of effective biocontrol action, and the opportunity to accurately position the biocontrol microbial agent in close proximity with the target pest (e.g., toxigenic fungi, insect pests, etc.). Other advantages are that using a spray formulation results in increased efficacy with a lower amount of bioplastic and biocontrol agent being required because the contact is better. Further, this sprayable formulation can be applied together with conventional products such as synthetic pesticides.

Mater-Bi™ is a bioplastic product composed of starch, polycaprolactone (ε-caprolactone), and a minor amount of a natural plasticizer (Bastioli, C. 2001. Starch/Starke 53:351-355). Mater-Bi™ is completely biodegradable having a rate of breakdown similar to that of cellulose (Bastioli, C. 1998. Polym. Degrad. Stabil. 59: 263-272). In addition to the highly favorable low environmental impact profile, its physical properties facilitate product handling and field application. We report a series of studies demonstrating the reliability of the novel sprayable bioplastic formulation for a biocontrol composition comprising a bioplastic matrix, Mater-Bi™ and a biocontrol microorganism. The composition of the invention encompasses a bioplastic dispersion product having the same identifying characteristics as Mater-Bi™ bioplastic granules with regard to the bioplastic of the Mater-Bi™ bioplastic granules; however, the characteristics of the formulation and of the applied bioplastic dispersion product are different as described above.

The effectiveness of novel sprayable bioplastic formulation for a biocontrol composition comprising a bioplastic matrix, Mater-Bi™ and a biocontrol microorganism has been demonstrated under controlled greenhouse conditions and confirmed under field conditions. The sprayable bioplastic biocontrol formulation is shown to be adaptable to the fungal and bacterial biocontrol agents, namely, *Trichoderma* and the non-toxigenic strains of *Aspergillus* and entomopathogenic isolates of *B. bassiana* and *B. thuringiensis*.

The method of the invention is applicable to any agricultural commodity which is grown for human consumption and/or which is damaged by fungal toxins and/or pathogens or pests, such as peanuts, corn, cotton, tree nuts, vegetable plants, and ornamental plants susceptible to damping off and root rot diseases.

For purposes of this invention, a fungal preparation or fungal agricultural biocontrol composition refers to a microbial preparation wherein the microbes comprise, consist essentially of, or consist of non-toxigenic or non-aflatoxigenic strains of *Aspergillus* and of *Trichoderma* strains capable of reducing aflatoxin contamination in agricultural crops and suppressing damping-off disease, respectively. The fungal preparations may contain one or more of non-toxigenic strains or non-aflatoxigenic strains of *Aspergillus*. Non-toxigenic strains of *Aspergillus* include any strain which does not produce the toxins aflatoxin and cyclopiazonic acid (CPA). The agricultural biocontrol composition for purposes of this invention includes a non-toxigenic strain or strains of fungi on agriculturally acceptable carriers, which may be any carrier which the fungi can be attached to and which are not harmful to the fungi or crops treated with the composition. The fungal preparation or fungal agricultural biocontrol composition has the ability to be biocompetitive when applied to soils growing agricultural commodities.

The non-toxigenic and non-aflatoxigenic strains of *Aspergillus* are sprayed onto plants in amounts effective to reduce toxin levels in agricultural commodities. As used herein "reduce toxin levels" refers to a reduction in amounts of toxin compared to that which would be expected in agricultural commodities which were not treated according to the methods of the present invention. Any accurate method of measuring and comparing toxin levels may be used for such comparisons as would be apparent to those skilled in the art.

As used herein, "in amounts effective, an amount effective or an effective amount" refer to the amount of the fungal preparation administered wherein the effect of the administration acts to reduce toxin contamination of agricultural commodities. The sprayed formulations are applied to the soil or parts of plants at a rate of approximately 0.75 to 7.5 kilograms (kg) per hectare (ha). The bioplastic formulation which can also contain added nutrients provides a protected environment which promotes growth and sporulation of the biocontrol fungi. The strains can be grown and applied as single strain sprayable compositions; or after the period of growth of the microorganisms with the bioplastic in liquid culture and the drying and milling process to obtain a finely-divided homogenous microorganism/bioplastic dispersion mixture, the dried products can be mixed in about equal proportions to provide a composition made up of different strains of *Aspergillus*.

EXAMPLES

Having now generally described this invention, the same will be better understood by reference to certain specific examples, which are included herein only to further illustrate the invention and are not intended to limit the scope of the invention as defined by the claims.

Example 1

Biocontrol Fungi, Bacterial, and Toxins

Laboratory and field studies were carried out with the following biocontrol microorganisms: *Beauveria bassiana* ATCC 74040, *B. bassiana* N18, *B. bassiana* GHA, *Trichoderma harzianum* ATCC 20847, *Aspergillus flavus* NRRL 30797 and insecticidal endotoxins produced by the bacteria *Bacillus thuringiensis* subsp., *kurstaki* HD1. Several microorganisms can be formulated with this sprayable bioplastic formulation, including *Metarhizium brunneum* (Erler et al. 2014. *Pest Manag. Sci.* 70:496-501), *Bacillus thuringiensis* subsp. *tenebrionis* (Elek et al. 1999. *J. Econ. EntomoL* 92:1062-1071), *Bacillus subtilis* (Hu et al. 2014. *Biol Control* 70:54-64), *Trichoderma hamatum* (Horst et al. 2005. *Plant Disease* 89:1195-1200), *Phoma macrostoma* (Bailey, K. L. 2010. *Canadian J. Plant Pathol.* 32:113-121) and *Myrothecium verrucaria* (Hoagland, et al. 2007. *Biocontrol Sci. Technol.* 17:721-731). *A. flavus* NRRL 30797 was deposited at the NRRL (National Center for Agricultural Utilization Research), 1815 N. University Street, Peoria, Ill. 61604, on Dec. 10, 2004, under the terms of the Budapest Treaty.

Example 2

Preparation of Sprayable Bioplastic-Based Formulations

The sprayable bioplastic formulation was prepared by homogenizing a mixture of bioplastic pellets, granules or powder in water (20%; w/v) in a Waring blender. After blending for 15 minutes, the bioplastic dispersion was passed through a 1-mm sieve, diluted (0.25-2.5% or other values) in water and stored at 4° C. until used. For specific requirements, such as addition of bioactive compounds or substances (i.e. endotoxins), the formulation can be sterilized by autoclaving for 15 min at 120° C. Alternatively, inoculation of the bioplastic powder can also be achieved by solid state fermentation processes where the bioplastic and, e.g., a fungal culture, are incubated together in a receptacle such as an autoclavable bag for 3-7 days, then dried in an oven at 45° C. The resulting dried material is ground into flour which is soluble in water and sprayable. The same result is obtained by passing bioplastic pellets or granules through an extruder equipped with small-size (<1 mm) nozzles. Bioplastic powder is then mixed with microbial propagules (e.g., spores, bacterial cells) or bioactive substances (e.g., endotoxins). Addition of nutrients or other chemicals (i.e. antibiotics, chemical pesticides, etc.) is optional.

Fungal isolates (e.g., *A. flavus*, *Trichoderma* spp., *B. bassiana*) were grown on potato dextrose agar until sporulation and then a number of ten 5-mm agar plugs were transferred into autoclavable plastic bags containing 1 kg of pre-wetted and autoclaved wheat seeds. Seeds were autoclaved for 30 min at 120° C. in three successive days. Bags were capped with cotton plugs fixed to steel rings and incubated in vertical position for 10 days at 28° C. Spores were recovered by transferring the entire mass into 1-L bottles containing 500 mL of a sterilized 0.2% Tween 20 solution. After shaking at 200 rpm for 30 min, spores were recovered by filtering the mixture through cheesecloth. After adjusting spore density using a hemocytometer, aliquots were added to the diluted bioplastic dispersion to achieve the desired potency (i.e. $10^7$ spores/mL or higher). The formulation can be directly used or stored at 4° C. A similar protocol is used to prepare a sprayable bioplastic dispersion formulation with bioactive ingredients. A description of the procedure for preparing a sprayable bioplastic formulation containing insecticidal endotoxin is reported below. The percentage of bioplastic and potency (number of spores, other propagules or bioactive compounds) of the final formulation can be modified as needed

Example 3

Application of Sprayable Bioplastic Formulation Under Controlled Greenhouse Conditions The feasibility of this sprayable bioplastic formulation to serve as a practical and effective formulation for microbial biocontrol agents was first evaluated under controlled greenhouse conditions. Plants of corn, cotton and soybean were grown in a greenhouse and watered daily from the soil for the whole duration of the experiment. A liquid dispersed starch-based bioplastic formulation prepared with 1% bioplastic powder (<1 mm) and $10^7$ spores/mL of *T. harzianum* ATCC 20847 or *A. flavus* NRRL 30797 was uniformly sprayed on the leaves, using a hand-sprayer. For each treatment, a total of 7 plants of each species were uniformly sprayed with 35 mL of formulation. Leaf samples were collected 1 hour before spraying and then 2 and 4 weeks after spraying, using a bleach-disinfected single hole punch. For each plant, a total of 5 samples were collected and transferred in sterile 2-mL tubes and directly used for DNA isolation, using the PowerSoil DNA isolation kit (MoBio Laboratories, Solana Beach, Calif.). Total recovered DNA was determined with the NanoPothometer P 360 (Implen GmbH, Munchen, Germany) and then target DNA was quantified by quantitative PCR, following the procedure described in Accinelli et al. (2012. *Crop Protection* 32:30-35). Briefly, PCR amplification was carried out in a total volume of 25 µL reaction containing 2 µL of DNA, 12.5 µL of 2× TaqMan Universal PCR Master Mix (Applied Biosystems Inc., Foster City, Calif.), and 0.2 µM of each of the primer pair. To quantify *T. harzianum* and *A. flavus* the primer pairs were Tf/uTr and omtB-F/omtB-R, respectively (Hagn et al. 2007. *J. Microbiol. Methods* 69:86-92; Kim et al. 2008. *Int. J. Food Microbiol.* 29: 49-60). Thermocycling conditions were as follows: 2 min at 50° C., 10 min at 95° C., and 40 cycles of 15 s at 95° C. and 1 min at 60° C. The resulting samples were analyzed using an ABI Prism 7700 Sequence Detection System (Applied Biosystem Inc.). After quantification, amplified fragment samples were subjected to melting-curve analysis. A standard curve was generated by plotting cycle threshold values (Ct) against logarithmic-transformed amounts of target DNA obtained from 10-fold dilutions of DNA isolated from spore dispersions of *T. harzianum* ATCC 20847 or *A. flavus* NRRL 30797.

As expected, after spraying the liquid bioplastic dispersion formulation containing spores of *T. harzianum* ATCC 20847 or *A. flavus* NRRL 30797, DNA from these two species was readily detectable. More specifically, 2 and 4 weeks after spraying, the amount of *T. harzianum* DNA recovered from corn leaves, was of 0.8 and 1.3 µg/mm$^2$ of leaf surface, respectively, and that of *A. flavus* of 1.1 and 2.5 µg/mm$^2$, respectively. Lesser values were found in cotton and soybean, with no differences between these two species. Average values for these two species, 2 and 4 days after spraying, were of 0.4 and 0.6 µg/mm² for *T. harzianum*, and 0.5 and 0.8 for *A. flavus*, respectively. Only a limited number (<5% of the analyzed samples) of leaf samples of the three untreated plant species, cotton, corn and soybean, had detectable amount of total DNA, with no traces of *A. flavus* or *T. harzianum* DNA. These findings are consistent with the concept that this sprayable bioplastic dispersion formulation was effective in adhering the two microbial biocontrol agents to the leaf surface and also in providing nutrients for their growth and sporulation.

Example 4

Field Experiment: Biocontrol of European Corn Borer in Corn

Experiments were conducted in a cereal-producing farm located in proximity of Bologna, Italy. Plots of 20 m×30 m were planted with a conventional corn hybrid (PR31K18; Pioneer Hi-Breed, Des Moines, Iowa) at the end of April 2012, and managed according to ordinary practices of the region. Each plot was surrounded by a 10-m wide buffer zone. At the V7 growth stage of corn, plots were sprayed with a 2.5% bioplastic sprayable formulation comprising conidia of the biocontrol isolate *B. bassiana* ATCC 74040 imbedded in the dispersed starch-based bioplastic or with the commercial formulation Naturalis (Intrachem Bio S.p.A., Italy). Naturalis is a liquid formulation containing 7% of active ingredient (spores of *B. bassiana* ATCC 74040). Both formulations were applied at the rate of 400 L/ha using a back pack sprayer. The experiment was carried-out according to a completely randomized block design with three replicates. An untreated control was also included. The whole experiment was repeated in 2013 following the same experimental procedures.

Flights of European Corn Borer females were monitored using commercial nylon-mesh cone traps (Riff98 s.r.l., Bologna, Italy). Traps were baited with lures of the sex pheromone of European Corn Borer ecotype E purchased from Isagro S.p.A. (Milan, Italy). A number of three traps were placed at the edges of each corn field and serviced weekly from end of May through the beginning of September. Lures were replaced following the manufacturer's instructions.

Damage caused by feeding activity of European Corn Borer larvae on vegetative components of corn plants was evaluated in mid July (first generation larvae) and at harvest (second generation larvae), following the procedure described in Mencarelli et al. (2013. *Pest Manag. Sci.* 69:1085-1091). In the case of damage produced by first generation larvae, a number of 30 plants were randomly selected from each plot and evaluated for presence (score 1) or absence (score 0) of the typical straight rows of shot holes (RSH). Damage severity was assessed in terms of number of RSH visually scored in each of the selected plants and rated on a 0-5 scale (0: no RSH; 1: 1-5 RSH; 2: 6-10 RSH; 3: 11-20 RSH; 4: 21-35; 5: >35 RSH). The same approach was adopted at harvest for evaluating injury caused by larvae tunneling into stalk, resulting in the formation of stalk cavities (SC). For SC, the following scale was used: 0: no SC; 1: 1-3 SC, 2: 3-5 SC, 3: 5-7 SC, 4: 7-9 SC, 5>9 SC. After evaluating SC, ears were removed and frequency of European Corn Borer-injured ears recorded.

At harvest, ears from all plants were hulled, dried at 50° C. for 72 hours, and yield recorded. Data were subjected to analysis of variance. Mean values were compared using Tukey's HSD test and significant differences were detected at the P>0.05 level. Data are expressed as mean±STD.

Figure 2:
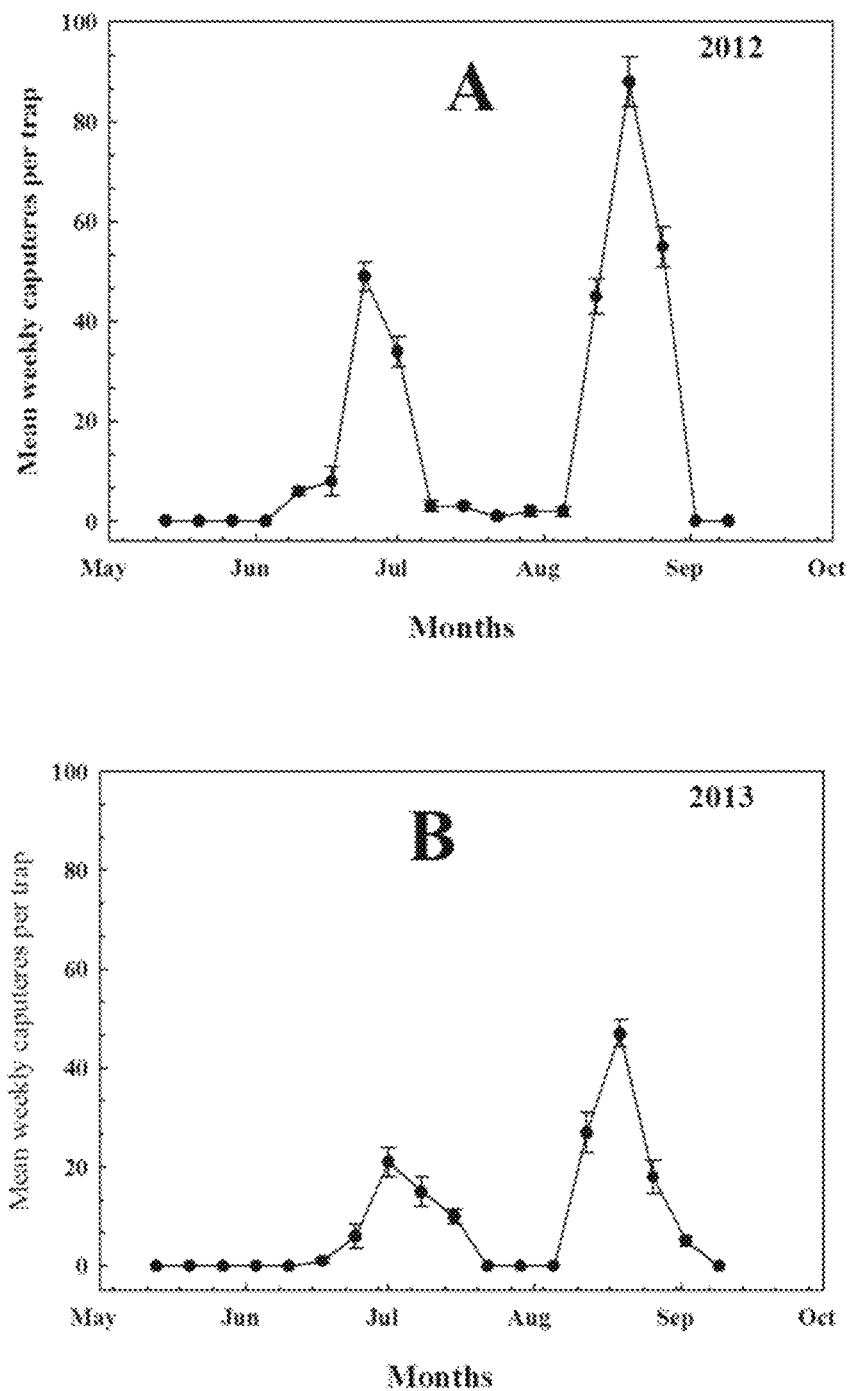
FIGS. 2A and 2B depict the capture of European Corn Borer moths during the 2012 (FIG. 2A) and 2013 (FIG. 2B) corn seasons.
Figure 3:
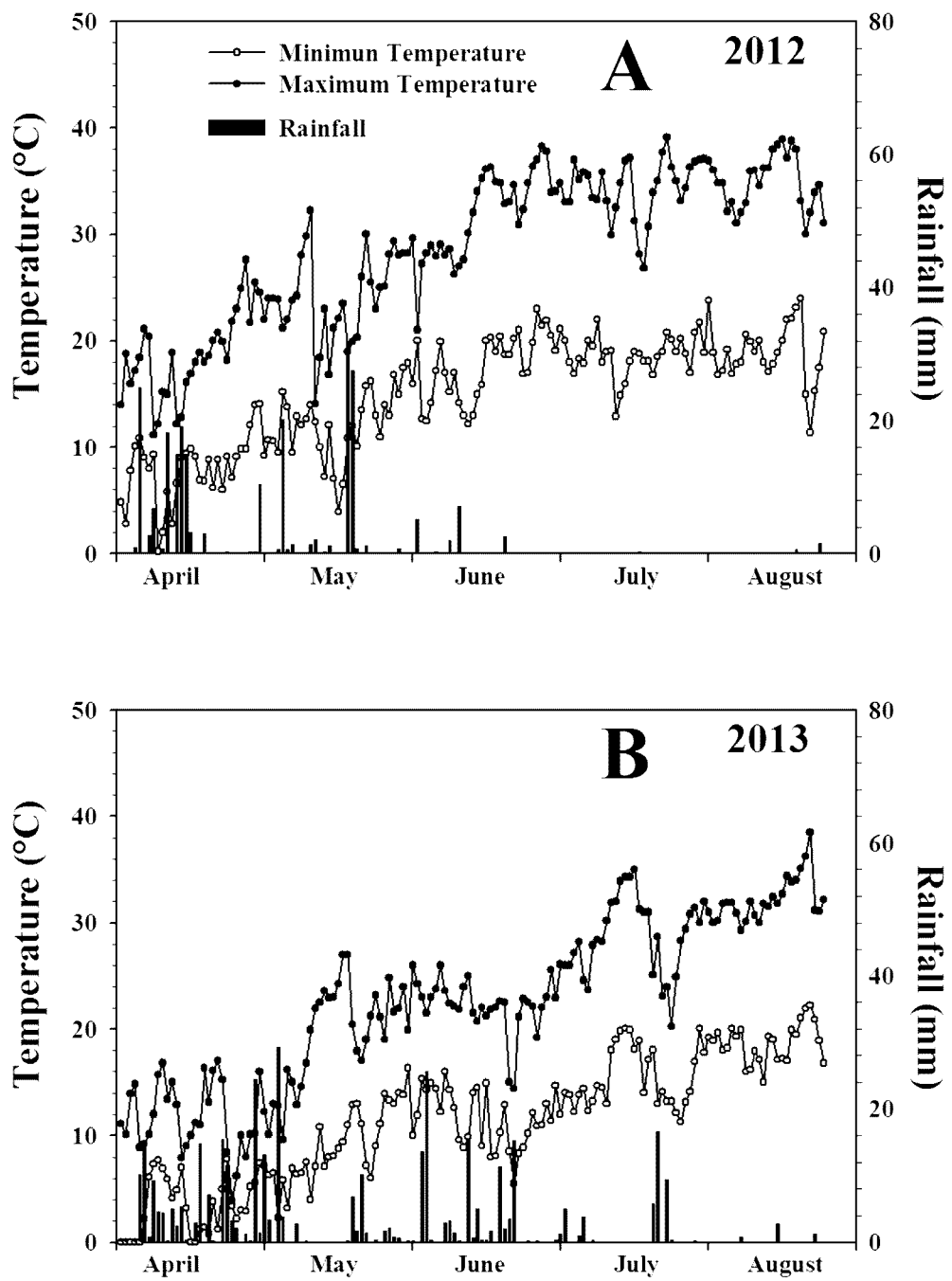
FIGS. 3A and 3B show the meteorological data (minimum/maximal temperature and rainfall) recorded during the 2012 (FIG. 3A) and 2013 (FIG. 3B) corn seasons.
Figure 4:
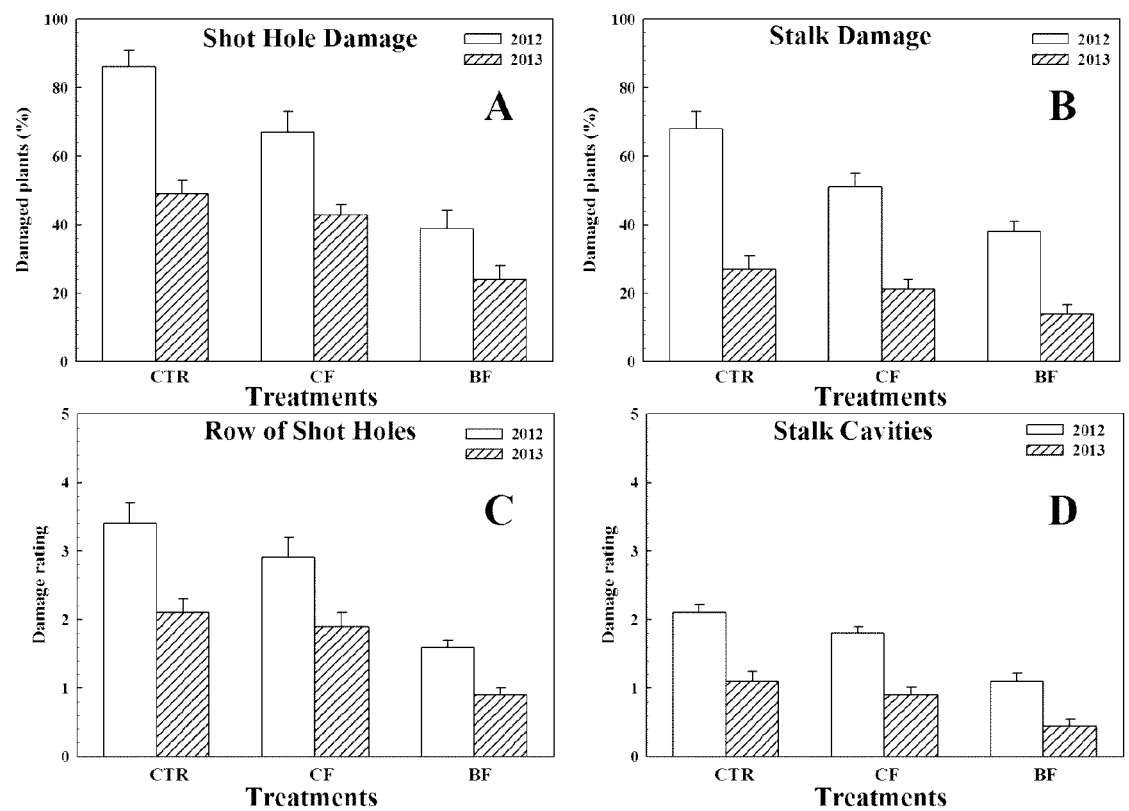
FIGS. 4A-4D depict the effect of control (CTR), commercial formulation (CF) and sprayable bioplastic formulation (BF) on damage frequency: shot hole damage (FIG. 4A) and stalk damage (FIG. 4B) and on intensity based on row of shot holes (FIG. 4C) and stalk cavities (FIG. 4D) resulting from feeding activity of the European Corn Borer on vegetative parts of corn plants during 2012 and 2013. Both formulations contained spores of *Beauveria bassiana*.

Captures of European Corn Borer moths are shown in FIGS. 2A and 2B. As observed in previous surveys, European Corn Borers showed a bivoltine phenology with two flight peaks, the first in late June and the second in late August. The number of weekly captures indicated a higher European Corn Borer infestation in 2012 (FIG. 2A) than in 2013 (FIG. 2B). This was likely due to the extremely hot and dry summer recorded in 2012 (FIG. 3A) in comparison to 2013 (FIG. 3B). Based on the life cycle of this key pest of corn, after egg hatch, early-instar larvae first feed on developing ears and whorl tissues. This feeding activity results in the formation of the characteristic RSH across the leaves. In 2012 and 2013, frequency of plants exhibiting RSH injury was of 86% and 49%, respectively (FIGS. 4A and 4B). Similar to the frequency of injured plants, damage intensity was higher in 2012 than in 2013 (FIGS. 4C and 4D). More specifically, the damage intensity rating was 3.4 and 2.1 in 2012 and 2013, respectively (FIGS. 4C and 4D).

In the first experimental year, application of the commercial formulation containing spores of *B. bassiana* ATCC 74040 resulted in a 22% decrease in the frequency of damaged plants with a damage rating of 2.9 (FIG. 4C). In 2013 the decrease was 12% with a damage rating of 1.9 (FIG. 4C). The percentage of plants exhibiting RSH damages was significantly reduced further, to lower percentages, in plots receiving the sprayable bioplastic-based formulation. More specifically, frequency and intensity of damages caused by first generation larvae in plants sprayed with bioplastic was respectively 39% and 1.6 in 2012, and 21% and 0.9 in 2013 (FIGS. 4A and 4C).

Beginning from the third larval stage, larvae bore into stalk producing stalk cavities (SC). In both years, percentage of plants exhibiting SC damages was lower with respect to RHS-injured plants (FIG. 4B). This was explained considering the well-known high mortality of early-stage European Corn Borer larvae. However, as observed with damages caused by larvae feeding on leaves, frequency and intensity of SC damages were higher in 2012 than in 2013. The 2.5% sprayable bioplastic formulation was significantly more effective in reducing damages on stalks with respect to the commercial formulation. More specifically, frequency and intensity of SC damages were reduced by 44% and 48% in 2012 and by 48% and 59 in 2013, respectively. Commercial formulation also reduced SC damages, but with a significantly lesser magnitude than the sprayable bioplastic (FIGS. 4B and 4D).

Figure 5:
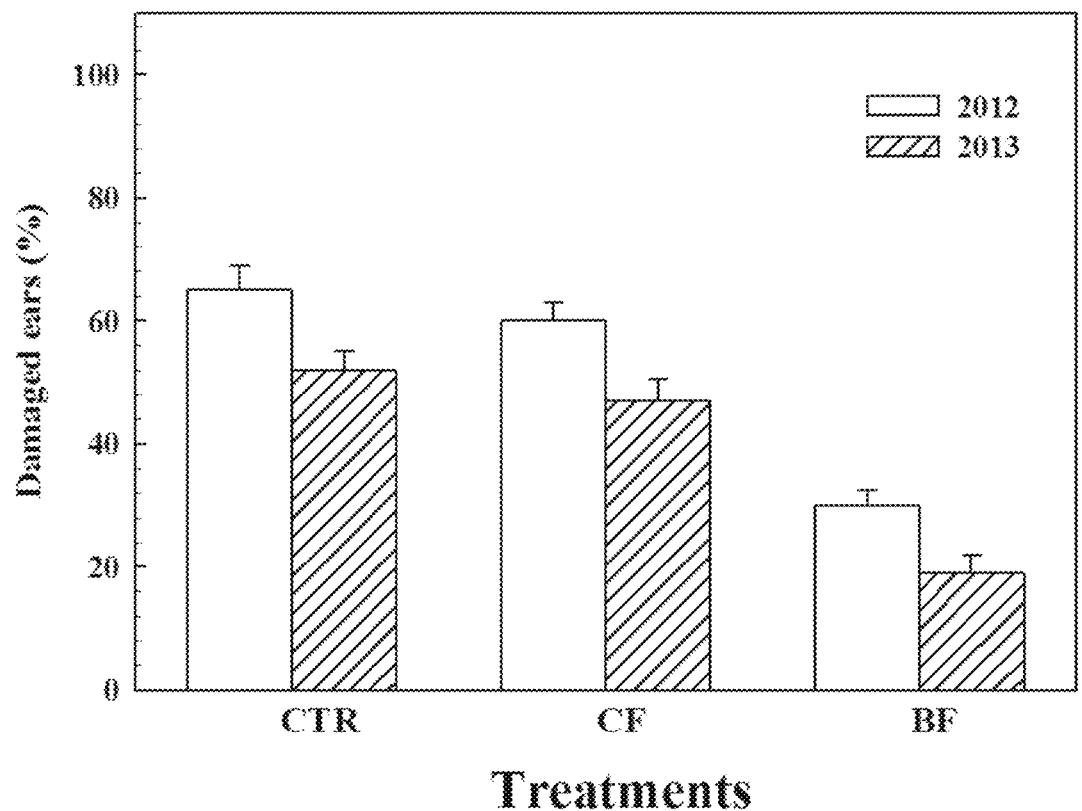
FIG. 5 depicts the effect of control (CTR), commercial formulation (CF) and sprayable bioplastic formulation (BF) on the percentage of ears showing damages resulting from feeding activity of European Corn Borer during 2012 and 2013.

In both of the two years, up to approximately half of the ears showed visible European Corn Borer damages. Damage was reduced by up to 8% with the commercial formulation and by up to 54% with the sprayable bioplastic (FIG. 5). Most importantly, application of sprayable bioplastic resulted in higher corn yield with respect to the untreated control and the commercial formulation. More precisely, in 2012, average corn yields of plots receiving the commercial and the bioplastic formulation were 6% and 35% higher than that in the untreated control, respectively. In 2013, these values were 8% and 43%, respectively. Thus, the sprayable bioplastic dispersion imbedded with the biocontrol agent *B. bassiana* was significantly more effective than the commercial formulation.

Example 5

European Corn Borer Bioassay

The potential of this sprayable bioplastic formulation to be ingested by target insect pests (i.e. European Corn Borer, ECB; *Ostrinia nubilalis*) was evaluated by insect bioassay. For this bioassay study, 2.5% sprayable dispersed bioplastic formulations were prepared as described above, except that fungal spores were replaced with endotoxins of *Bacillus thuringiensis* subsp. *kurstaki*, strain HD1 within the bioplastic dispersion. Insecticidal endotoxins were obtained from a commercial formulation as described in Accinelli et al. (2004. *Agric. Ecosys. Environ.* 103:497-507). Briefly, 50 g of Dipel 2× (Sipcam S.p.A., Pero, Italy) was initially washed with 1 M sodium chloride and then with deionized water. Each washing was repeated two times. Washed sediments were extracted with a MOPS buffer (0.1 M 3-N-morpholino-propanesulfonic acid, pH 7.8) containing 0.5 M dithiothreitol and 1 M potassium thiocyanate and then dialyzed for 8 hours against deionized water and precipitated using ammonium sulfate. Precipitate was centrifuged at 27,000 g and resuspended in deionized water. Concentration of the stock solutions used for preparing sprayable bioplastic formulations was calculated after quantification the endotoxins with the Lowry method.

Insect bioassays were conducted as described in Accinelli et al. (2004, supra). Briefly, 10 mL of insect diet was added to each cell of a 50-cell bioassay tray and four-instar European Corn Borer larvae were transferred to the cells (1 larvae/cell). Cells were closed with a perforated plastic lid and placed in a climatic chamber at 27° C. and a photoperiod of 16:8 (light:dark). After 3 days of incubation, larvae were transferred to cells sprayed with 2.5% sprayable dispersed bioplastic formulations prepared with increasing concentration of endotoxins (0.1, 1 and 10 µg/mL). After 6 hours, larvae were then replaced in the cells filled with the specific diet. A total of 30 larvae were used for each concentration. Insect mortality was scored after 14 days.

Figure 6:
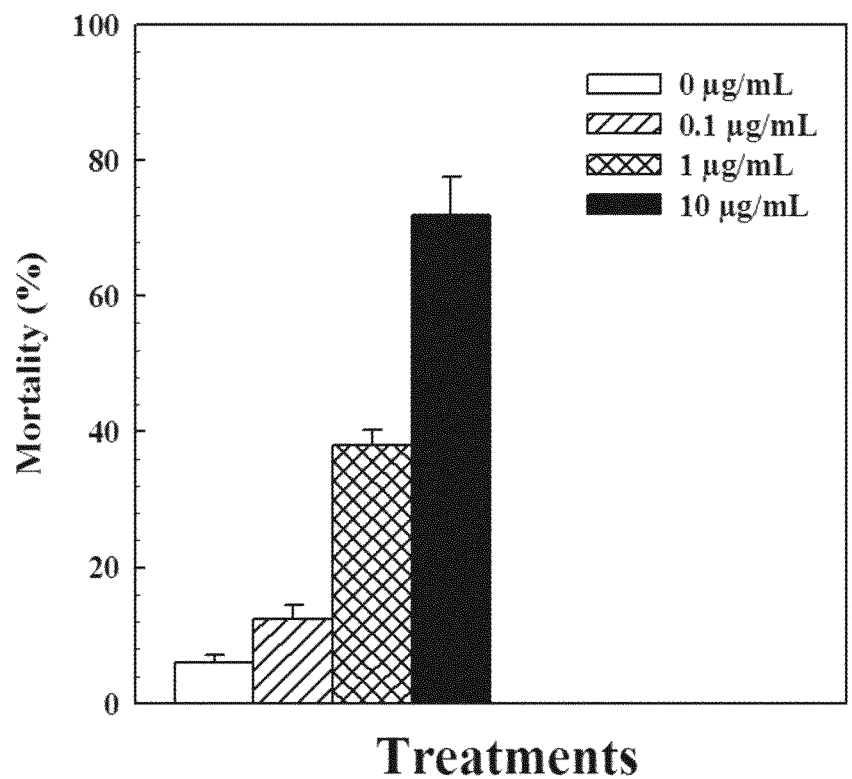
FIG. 6 depicts the mortality of second-instar European Corn Borer larvae after incubation for 6 hours in cells sprayed with a 2.5% sprayable bioplastic formulation comprising dispersed starch-based bioplastic imbedded with different concentrations of *Bacillus thuringiensis* subsp. *kurstaki* endotoxins.

Results of the European Corn Borer bioassay are shown in FIG. 6. The increasing mortality of larvae transferred for 6 hours in cells containing only dried bioplastic prepared with increasing concentration of endotoxins clearly demonstrated the capability of this formulation to be ingested by European Corn Borer larvae. Basically, the concept behind the present invention is that after water evaporation, a thin layer of the inoculated bioplastic formulation remains adherent to the leaf surface (FIG. 1), where it serves as a growth substrate for the biocontrol microorganism but also has the potentiality to be ingested by target insect pests. This latter aspect is expected to increase the activity against target pests.

Example 6

Biocontrol of *Aspergillus flavus* in Corn

Experiments were conducted in 2012 in the farm mentioned above and followed the same experimental scheme and procedures. At the V7 growth stage of corn (where plants are at the seven leaf stage), plots were sprayed with a 1% bioplastic liquid formulation comprising spores of the biocontrol isolate *A. flavus* NRRL 30797 ($10^7$ spores/mL) imbedded in the bioplastic dispersion and applied at the rate of 400 L/ha, using a back pack sprayer. As with the European Corn Borer biocontrol experiment, the current experiment was carried out according to a completely randomized block design with three replicates. At harvest, 60 ears of corn were randomly collected from each plot, shelled and dried at 50° C. for 72 hours and ground (<1 mm) for chemical analysis. After extraction with methanol/water (70:30), chemical analyses were performed by HPLC following the procedure described in Accinelli et al. (2012, supra). Data were subjected to analysis of variance. Mean values were compared using Tukey's HSD test and significant differences were detected at the P>0.05 level. Data are expressed as mean±STD.

Figure 7:
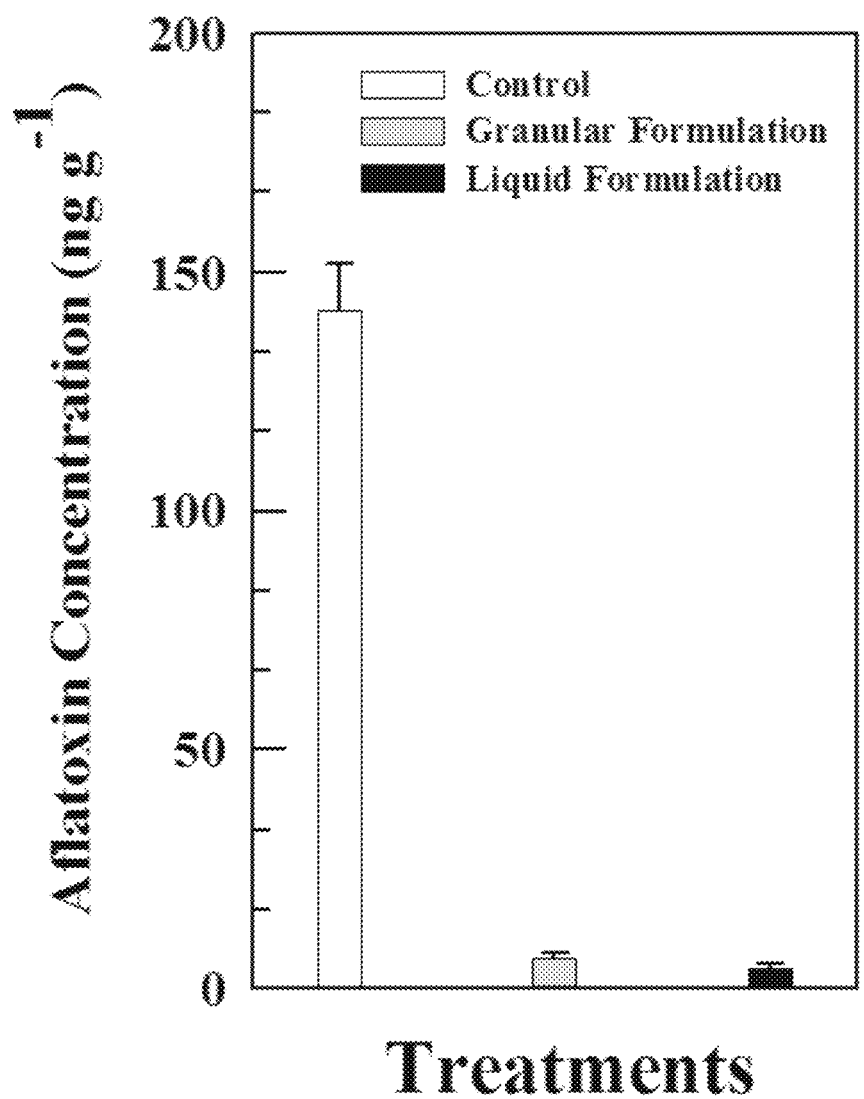
FIG. 7 shows the effect of the sprayable dispersed bioplastic formulation on aflatoxin contamination in corn in comparison with bioplastic granules and untreated control.

The hot and dry conditions recorded during the 2012 corn growing season were also conducive to *A. flavus* infestation of corn (FIG. 3A). In untreated control plots the average aflatoxin contamination was 140 ng/kg. Application of the sprayable bioplastic formulation resulted in an approximately 97% reduction in aflatoxin levels (FIG. 7). These findings show that this sprayable formulation is highly effective in reducing aflatoxin contamination in corn.

Example 7

Biocontrol of Damping-Off of Seedlings

The same concept used for spraying microbial biocontrol agents on plant leaves was extended for protecting seedlings from damping-off agents. More specifically, a sprayable bioplastic-based formulation was used to control damping-off in tomato seedlings caused by the fungus *Rhizoctonia solani*. Tomato seeds (*Lycopersicum escultentus* 'ACE 55 VF'; Blumen s.r.l., Milan, Italy) were sprayed with a 2.5% bioplastic formulation comprising spores of the biocontrol fungus *T. harzianum* ATCC 20847 (final potency $10^8$ spores/mL) imbedded in a dispersed starch-based bioplastic. Seeds were transferred into a benchtop rotative siever and sprayed using a hand-sprayer. Treated seeds were dried for 1 hour and then directly planted in seedling trays filled with infested potting mix prepared as follows. A sufficient mass of the potting mix Terraplant 2 (Torf-un Humuswenk Uchte GmbH, Uchte, Germany) was infested with *R. solani* NRRL 22805 supplied as pathogen-infested pulverized grains. Briefly, four 3-mm agar plugs from actively growing cultures of the fungal pathogen on PDA were placed into 250-mL bottles containing barley grains (25 g of grains and 18 mL of water) that had been autoclaved three times at successive days. Bottles were incubated at 25° C. in the dark. After a 2-week incubation, grains were pulverized, passed through a 2-mm sieve and incorporated into the potting mix. After thorough mixing, potting mix was stabilized by incubation at 25° C. The *Rhizoctonia*-infected growth substrate was mixed with non-infected potting mix to achieve desired disease incidence. Tray cells (5-cm diameter; 5-cm depth) were planted with sprayed or non-sprayed tomato seeds and incubated in a growth chamber at 25° C. supplemented with light for a 12-h period. A total of 300 seeds were planted for single treatment. Trays filled with non-infested potting mix were included as controls. The experiment was arranged in a completely randomized block design with three replicates and the plant stand was monitored for 18 days.

Figure 8:
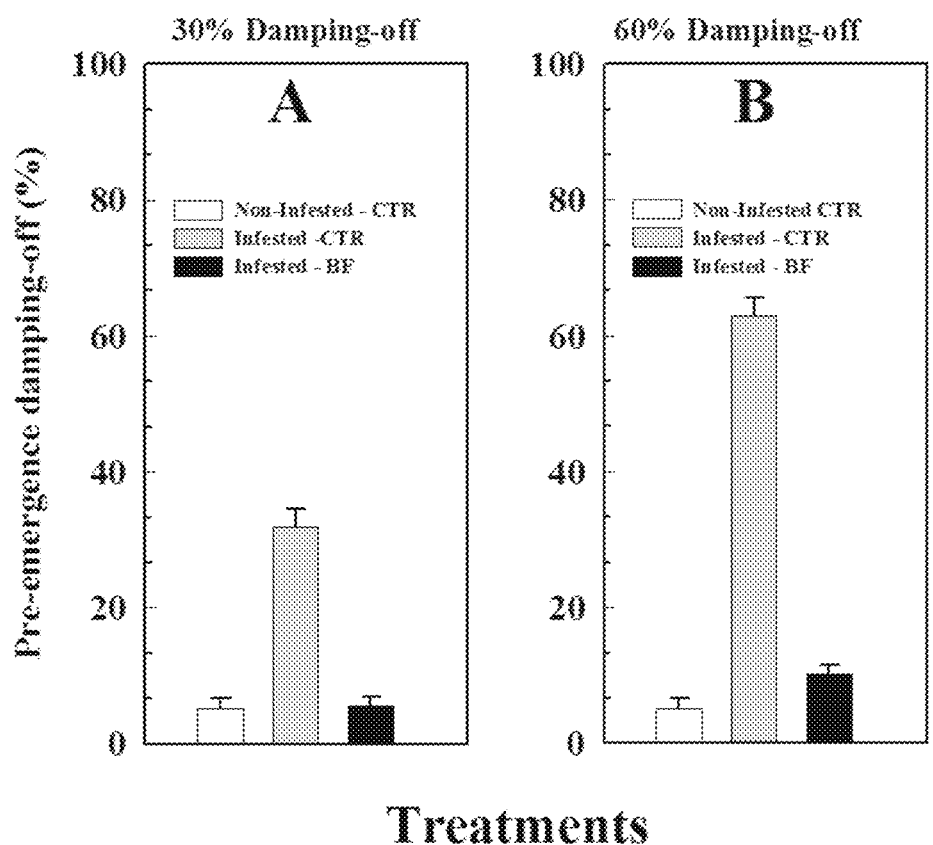
FIGS. 8A and 8B show the effect of spraying a 2.5% sprayable dispersed starch-based bioplastic formulation containing spores of *Trichoderma harzianum* on the surface of seeds on their emergence. Seeds were planted in a pot mix which was infested with two different levels of *Rhizoctonia solani* infestation causing 30% (FIG. 8A) and 60% (FIG. 8B) damping-off.

Application of the sprayable bioplastic formulation was effective in reducing damping-off of tomato seedlings. More specifically, when sprayed seeds were planted in a potting mix with a level of pathogen infestation corresponding to 30% damping-off, pre-emergence damping-off was reduced by up to 85% with respect to non-sprayed seeds (FIG. 8A). Seeds were also protected when planted in pot mixtures with an even more severe level of infestation. As shown in FIG. 8B, when tomato seeds were planted in a potting mix artificially infested with *R. solani* to achieve 60% damping-off, the incidence of unemerged seeds was approximately 10%. These findings showed that by forming a sticky envelope around the seeds, this sprayable formulation protected tomato seedlings from damping-off caused by *R. solani*.

Example 8

Biocontrol of the Tarnished Plant Bug in Cotton

Sprayable bioplastic formulations with an increasing percentage of bioplastic were prepared following the procedures described in [0034] and [0035] and evaluated for the delivery of spores of two biocontrol isolates, *Beauveria bassiana* N18 and *B. bassiana* GHA, with the final objective to control of Tarnished Plant Bug (TPB; *Lygus lineoraris*) infestation in cotton.

Preliminary insect bioassay experiments were carried-out to evaluate the feasibility of dispersed bioplastic formulations containing increasing amounts of bioplastic powder (0.25, 0.50, 0.75 and 1% w/v) and spores of *B. bassiana* N18 ($10^9$ spores/mL) to control *Lygus lineolaris*. Dispersed bioplastic formulations were compared with a 0.04% solution of Tween 80 and water control. Bioassays were conducted following the procedure described in Portilla et al. (2011. *J. Insect Sci.* 11:1-10). Briefly, aliquots of 6 mL of a spore dispersion containing 0.5 g spores were diluted in the 0.04% Tween 80 water solution or sprayable dispersed bioplastic to achieve a concentration of $6 \times 10^9$ spores/mL. For each treatment (Tween 80 or dispersed bioplastic formulations), 90 insects were evaluated. Formulations were sprayed using pressurized laboratory equipment. After spraying TPB adults were transferred into an insect observation cage (BioQuip 1466A) to let them dry. Sprayed insects were knocked down individually into Solo cups filled with artificial solid diet. Adults were examined daily for mortality. Dead insects were kept in the same cup and were daily checked for fungal sporulation. More specifically, adults and nymphs were held in an environmental room at 27° C., 65% R.H., and 12:12 hours (L:D) photoperiod for 10 days.

Figure 9:
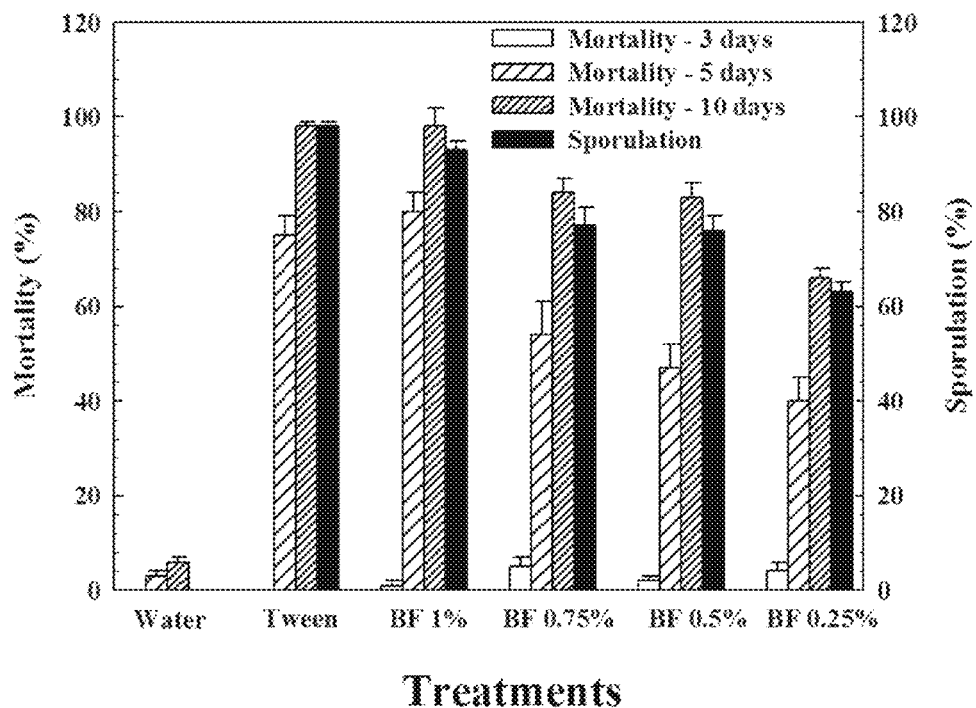
FIG. 9 shows the effect of *B. bassiana* formulated as sprayable dispersed starch-based bioplastic on mortality and infection of Tarnished Plant Bug adults. Bioplastic formulations (BF) were prepared with varying amount of bioplastic (1, 0.75, 0.5 and 0.25% w/v) and evaluated against 0.04% Tween 80 and water control.

After 3 days from spraying, no differences in TPB mortality were observed between TPB receiving the bioplastic dispersion and the Tween 80 treatment. As expected, low mortality (<0.5%) was observed after spraying with water. Five days after *B. bassiana* application, TPB mortality was of 80.0 and 75.5, for 1% dispersed bioplastic formulation and 0.04% Tween-80, respectively. Application of bioplastic formulations prepared with 0.75, 0.5 and 0.25% bioplastic, resulted in mortality of 46.6, 54.4, 40.0, respectively. Higher mortality was observed 10 days after sprayed bioplastic or Tween-80 on TPB adults. More specifically, mortality was of 97.7%, with no differences among 1% bioplastic and 0.04% Tween 80. With 0.75, 0.5 and 0.25% bioplastic, mortality was of 83.3, 84.4, and 66.6%, respectively (FIG. 9). The dispersed bioplastic formulation also promoted fungal sporulation. After 10 days from spraying, sporulation was of approximately 95%, with no differences among 1% bioplastic and Tween 80. With 0.75, 0.5 and 0.25% bioplastic, sporulation was of 76.6, 77.7, and 63.3, respectively.

Figure 10:
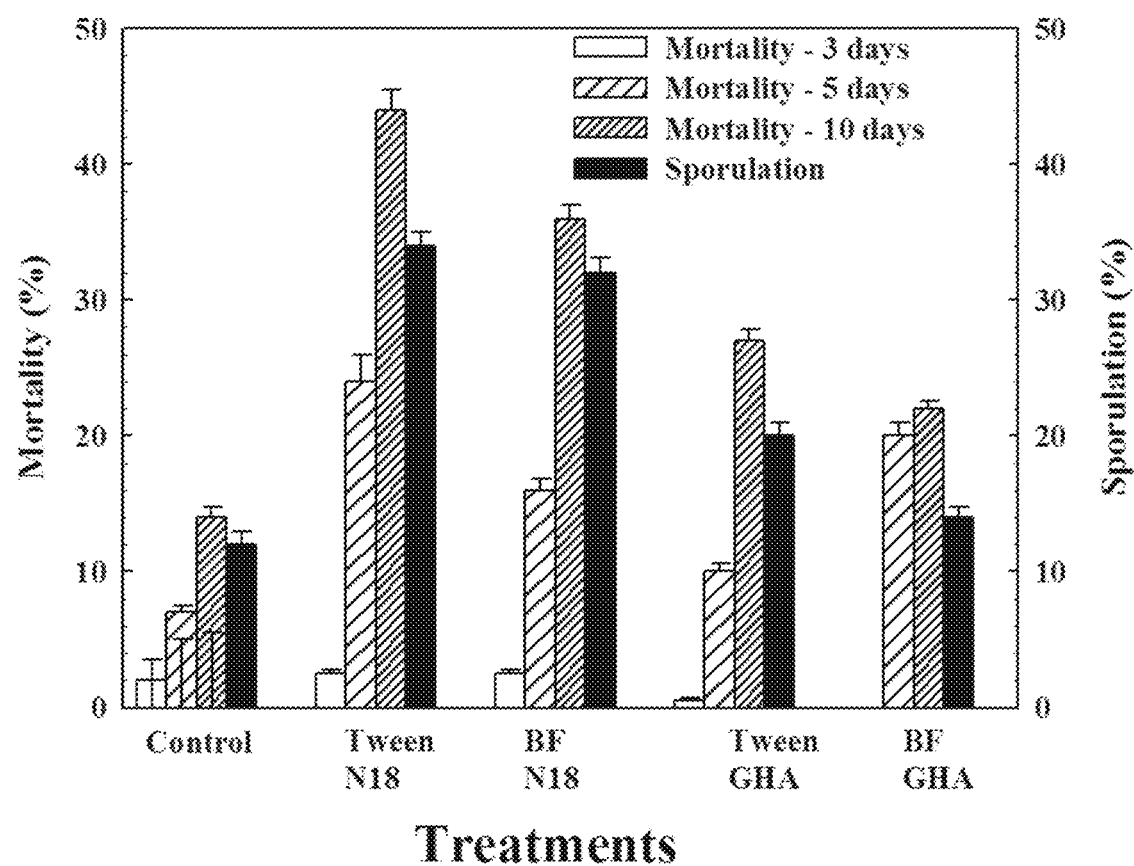
FIG. 10 shows the effect of *B. bassiana* formulated as 1% sprayable dispersed starch-based bioplastic (BF) on mortality and infection of Tarnished Plant Bug adults under field condition. Bioplastic formulations were sprayed on plots planted with cotton and evaluated against 0.04% Tween 80 and untreated control. Two *B. bassiana* strains, N18 and GHA, were used for preparing BF and Tween 80 formulations.

The sprayable bioplastic-based biocontrol formulation was also evaluated in a large field study consisting of 50 plots (270 m$^2$; 18 m long and 15 m wide). In this study, 1% bioplastic formulations containing the isolate *B. bassiana* N18 or *B. bassiana* GHA, were sprayed on cotton plants in July 2013. Treatments were carried-out using a pressurized multi-sprayer (Cone-Tip Quick TXVS12) mounted on a John Deere tractor at the pressure of 90 psi and at the speed of 8 km/hr, with a volume of 30 L per hectar. Five days after treatment, TPB mortality in plots sprayed with 1% bioplastic/N18 and 0.04% Tween 80/N18 was of 36, and 44%, respectively. Strain GHA was less effective in controlling TPB infestation in cotton. More specifically, application of 1% bioplastic/GHA and 0.04% Tween 80/GHA resulted in a TPB mortality of 22 and 27%, respectively. A mortality of 14% was observed in untreated control plots (FIG. 10).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A sprayable liquid biocontrol formulation comprising a dispersed starch-based bioplastic growth substrate obtained by homogenizing any one or more of different types of bioplastic matrices including granules, pellets or powder in water or by extruding said different types of bioplastic matrices into water, wherein said dispersed starch-based bioplastic growth substrate is then imbedded, enriched or inoculated with biocontrol microorganisms, wherein said sprayable liquid biocontrol formulation has the properties of adhering said biocontrol microorganisms to plant and seed surfaces and of retarding breakdown of said dispersed starch-based bioplastic growth substrate and of also retarding breakdown of said embedded biocontrol microorganisms thus ensuring that said biocontrol microorganisms remain as a durable control of pests and that the dispersed starch-based bioplastic growth substrate remains as a prolonged growth substrate for said biocontrol microorganisms, thereby resulting in increasing numbers of said biocontrol microorganisms over time when compared to those numbers of biocontrol microorganisms deposited at the initial time of spraying.

2. The sprayable liquid biocontrol formulation of claim 1, wherein said adhering results in a visible film on said plant and seed surfaces.

3. The sprayable liquid biocontrol formulation of claim 1 wherein the biocontrol microorganism is a non-toxigenic strain of *Aspergillus flavus*.

4. The sprayable liquid biocontrol formulation of claim 1 wherein the biocontrol microorganism is the non-toxigenic *A. flavus* strain NRRL 30797.

5. The sprayable liquid biocontrol formulation of claim 1 wherein the biocontrol microorganism is *Trichoderma harzianum* or *Trichoderma virens*.

6. The sprayable liquid biocontrol formulation of claim 1 wherein the biocontrol microorganism is an isolate of *Beauveria bassiana*.

7. The sprayable liquid biocontrol formulation of claim 1 wherein the biocontrol microorganism is an endotoxin produced by *Bacillus thuringiensis*.

8. A method of reducing aflatoxin contamination of corn by applying the sprayable liquid biocontrol formulation of claim 3 to the plant or soil to control aflatoxin contamination.

9. A method of reducing aflatoxin contamination of corn by spraying the sprayable liquid biocontrol formulation of claim 4 onto the soil, plants or plant parts to control aflatoxin contamination.

10. A method of suppressing damping off in plants susceptible to damping off comprising spraying the sprayable liquid biocontrol formulation of claim 5 onto soil, plants or plant parts to control damping-off disease.

11. A method of controlling infestation by the European Corn Borer (*Ostrinia nubilalis*) comprising spraying the sprayable liquid biocontrol formulation of claim 6 to control the European Corn Borer.

12. A method of controlling infestation by the European Corn Borer comprising spraying the sprayable liquid biocontrol formulation of claim 7 to plants to control the European Corn Borer.

13. A method of controlling infestation by the Tarnished Plant Bug (*Lygus lineoraris*) in cotton comprising spraying the sprayable liquid biocontrol formulation of claim 6 to control the Tarnished Plant Bug in cotton.

\* \* \* \* \*